US006845329B1

(12) United States Patent
Low

(10) Patent No.: US 6,845,329 B1
(45) Date of Patent: Jan. 18, 2005

(54) PROCESS FOR DETERMINING A ZEOLITE STRUCTURE AND ITS CORRESPONDING ADSORPTION ISOTHERM

(75) Inventor: John J. Low, Schaumburg, IL (US)

(73) Assignee: UOP LLC, Des Plaines, IL (US)

( * ) Notice: Subject to any disclaimer, the term of this patent is extended or adjusted under 35 U.S.C. 154(b) by 247 days.

(21) Appl. No.: 10/103,503

(22) Filed: Mar. 20, 2002

Related U.S. Application Data

(60) Provisional application No. 60/292,003, filed on May 18, 2001.

(51) Int. Cl.$^7$ ............................................. C01B 33/26
(52) U.S. Cl. ...................................... 702/27; 423/328.2
(58) Field of Search .................. 702/27, 28; 423/328.2, 423/710, 702, 239.2, 648.1; 585/481; 502/243; 95/130

(56) References Cited

U.S. PATENT DOCUMENTS

| | | | | |
|---|---|---|---|---|
| 4,973,785 A | * | 11/1990 | Lok et al. | 585/481 |
| 5,185,138 A | * | 2/1993 | Vaughan et al. | 423/710 |
| 5,328,675 A | * | 7/1994 | Vaughan et al. | 423/328.2 |
| 5,622,684 A | * | 4/1997 | Pinnavaia et al. | 423/702 |
| 6,024,935 A | * | 2/2000 | Mills et al. | 423/648.1 |
| 6,423,121 B1 | * | 7/2002 | Kiyama et al. | 95/130 |
| 2002/0052290 A1 | * | 5/2002 | Bowman et al. | 502/243 |
| 2003/0103887 A1 | * | 6/2003 | Stephenson | 423/239.2 |

OTHER PUBLICATIONS

Low et al., Modeling the Seperation of Air on Zeolites, Oct. 23, 2002, UOP Reasearch center, All pages.*
Hans G. Dehmelt, Experiments with an Isolated Subatomic Particle at Rest, Dec. 8, 1989, University of Washington Department of Physics, All pages.*
Dr. John L. Falconer, Heterogeneous Catalysis, Dec. 30, 2001, The University of Colorado, all published papers.*
The Reasearch Foundation et al., Learning Experiences for Synthetic Zeolite ZSM–5, Dec. 30, 1989, SUNY, All pages.*
F. A. Franz, Rubidium Spin Relaxation in The Rare Gases Under Ultraclean Conditions Abstract, Mar. 8, 1965, Physics Review 139, A603 to A611.*
Hans Dehmelt, The Ion Penning Trap, Oct. 12, 1989, Press Release of The 1989 Nobel Prize in Physics, All pages.*
Dr. Kyesang Yoo, The Development of Clear Catalyst for Alkylaton of Isobutane with 2–Betene, Aug. 15, 2003, University of Cincinnati, All pages.*
GULP–A Computer Program for the Symmetry Adapted Simulation of Solids, J D. Gale, Journal of the Chemical Society, Faraday Trans., 93, 629–637 (1997).
DISCOVER–http://www.accelrys.com/cerius2/C2_discover.html.
OFF (Open Force Field)—http://www.accelrys.com/cerius2/C2_open_ffield_us_data.pdf.
Low, J.J., Sherman, J.D., Cheng, L.S., Patton, R.L., Gupta, A., Snurr, R.Q.; Presented at the $7^{th}$ International Conference on Fundamental of Adsorption, Nagasaki, Japan, May 2001.

* cited by examiner

Primary Examiner—John Barlow
Assistant Examiner—Victor J. Taylor
(74) Attorney, Agent, or Firm—John G. Tolomei; Frank S. Molinaro

(57) ABSTRACT

Applicant has developed a method for predicting the structure of a zeolite including the cation positions and distributions. The method comprises using combinatorial minimization and molecular mechanics techniques. One important aspect of the technique is the bumping of two cations. Another aspect of the invention is predicting the adsorption isotherms of the invention using a biased-Grand Cononical Monte Carlo technique which contains electrostatic and dispersion interaction terms between gas molecules and the zeolite.

3 Claims, 3 Drawing Sheets

PROCESS FOR DETERMINING A ZEOLITE STRUCTURE AND ITS CORRESPONDING ADSORPTION ISOTHERM

CROSS-REFERENCE TO RELATED APPLICATION

This application claims priority of U.S. Provisional Application No. 60/292,003 filed on May 18, 2001, the contents of which are incorporated in their entirety by reference.

FIELD OF THE INVENTION

This invention relates to a method for determining the structure of a zeolite including cation locations. Once the location of the cations is determined, the corresponding adsorption isotherm can be calculated. The invention also relates to a computer readable storage medium containing computer executable code for instructing a computer to carry out the method Finally, the invention relates to a storage device tangibly containing computer instruction to carry out the method

BACKGROUND OF THE INVENTION

Zeolites are crystalline aluminosilicate compositions which are microporous and which have a three-dimensional oxide framework formed from corner sharing $AlO_2$ and $SiO_2$ tetrahedra. Numerous zeolites, both naturally occurring and synthetically prepared are used in various industrial processes. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure.

One important process which uses zeolites is the separation of nitrogen from air using Pressure Swing Adsorption (PSA). The types of zeolites which are used for air separation are low silica zeolites such as those having the faujasite topology (FAU) and having a $SiO_2/Al_2O_3$ of less than 3.0 and preferably about 2.0. Considerable effort has been expanded in order to develop adsorbents with improved selectivities for nitrogen versus oxygen. However, these efforts have resulted in only incremental improvements.

In view of the expense and somewhat low return of this research, it would be very beneficial to develop a method which could accurately predict the structure (especially the extra-framework cations) and adsorption isotherms of zeolites. Development of such a method requires knowing the physics of air separation in low silica zeolites. It is known from the art that the energy of adsorption is the sum of dispersion, electrostatic and induction terms. $N_2$ has a larger quadruple moment than $O_2$ which causes $N_2$ to have a larger heat of adsorption than $O_2$ on low silica zeolites. The larger adsorption heat causes low-silica zeolites to be more selective for $N_2$ than $O_2$. An adsorbent with a larger void volume is advantageous because it can adsorb more sorbate molecules. This allows the adsorbent to maintain selectivity at higher loadings. In spite of the simplicity of calculating adsorption energy, the state of the art in predicting structure and properties of zeolites cannot predict the relative performances IS of materials for air separation. Fairly high levels of accuracy are needed to predict the relative performance. An error of 0.1 kcal/mol in the free energy of adsorption leads to errors~15% in loadings at room temperature. This level of accuracy is required to predict relative performance. Current methods of predicting performance do not yield results with 0.1 kcal/mol accuracy.

Applicant has developed a method which accurately predicts zeolite structure including the cation locations and further determines the adsorption isotherms for these zeolites. A key feature of the method is that it can accurately predict the location of the cations. Cation location is important because $N_2$ has a larger quadruple moment that $O_2$. This larger moment interacts favorably with the large electric field gradient near the cation resulting in $N_2$ being selectively adsorbed on the cations. Accordingly, a method which can predict the number and position of exposed cations on a zeolite can determine the relative selectivity of the zeolites without synthesizing them, thus quickly narrowing potential candidates.

SUMMARY OF THE INVENTION

As stated, the instant invention relates to a zeolite structure comprising a three-dimensional framework of $AlO_2$ and $SiO_2$ tetrahedral units and extra-framework cations, the method comprising:

a) placing one cation at a time onto vertices of a grid and calculating the lowest potential energy position for the cation and continuing to add cations until the negative charge of the framework is balanced;

b) bumping two cations during each step of a combinatorial minimization technique to obtain the lowest potential energy distribution of all the cations;

c) performing molecular mechanics calculations to obtain the lowest energy cation positions on a fixed zeolite geometry for the cation distribution of step (b);

d) moving each cation which is within 0.1Å of its crystallographic special position to its special position; generating the symmetrically equivalent sites from the cation positions of all the cations and determining the minimum energy for the cations on the sites using combinatorial minimization techniques, with bumping;

e) optimizing the geometry of the framework and cation sites simultaneously to the closest local minimum; and f) repeating steps (a) to (e) at least once to obtain an optimized zeolite structure.

Another embodiment of the invention is a computer readable storage medium containing computer executable code for instructing a computer to carry out the above described method.

Yet another embodiment is a storage device tangibly containing computer instructions to carry out the method.

The invention also relates to a method for predicting adsorption isotherms starting with a zeolite structure obtained by the above method. The method involves introducing gas molecules into the zeolite structure using a biased-Grand Cononical Monte Carlo technique containing electrostatic interactions and dispersion interactions between the gas molecules and the zeolite. This technique can predict the loading of the gas molecules in the zeolite at various pressures and temperature The electrostatic interaction between the zeolite and the gas molecules is obtained using a multi-polar expansion of the charge distribution from a band structure calculation of the zeolite. A Morse-Spline-Van der Waals potential fit to experimental data is used to obtain the dispersion interaction between the zeolite structure and gas molecules.

These and other objects and embodiments will become clearer after a detailed description of the invention.

DETAILED DESCRIPTION OF THE INVENTION

Figure 1:
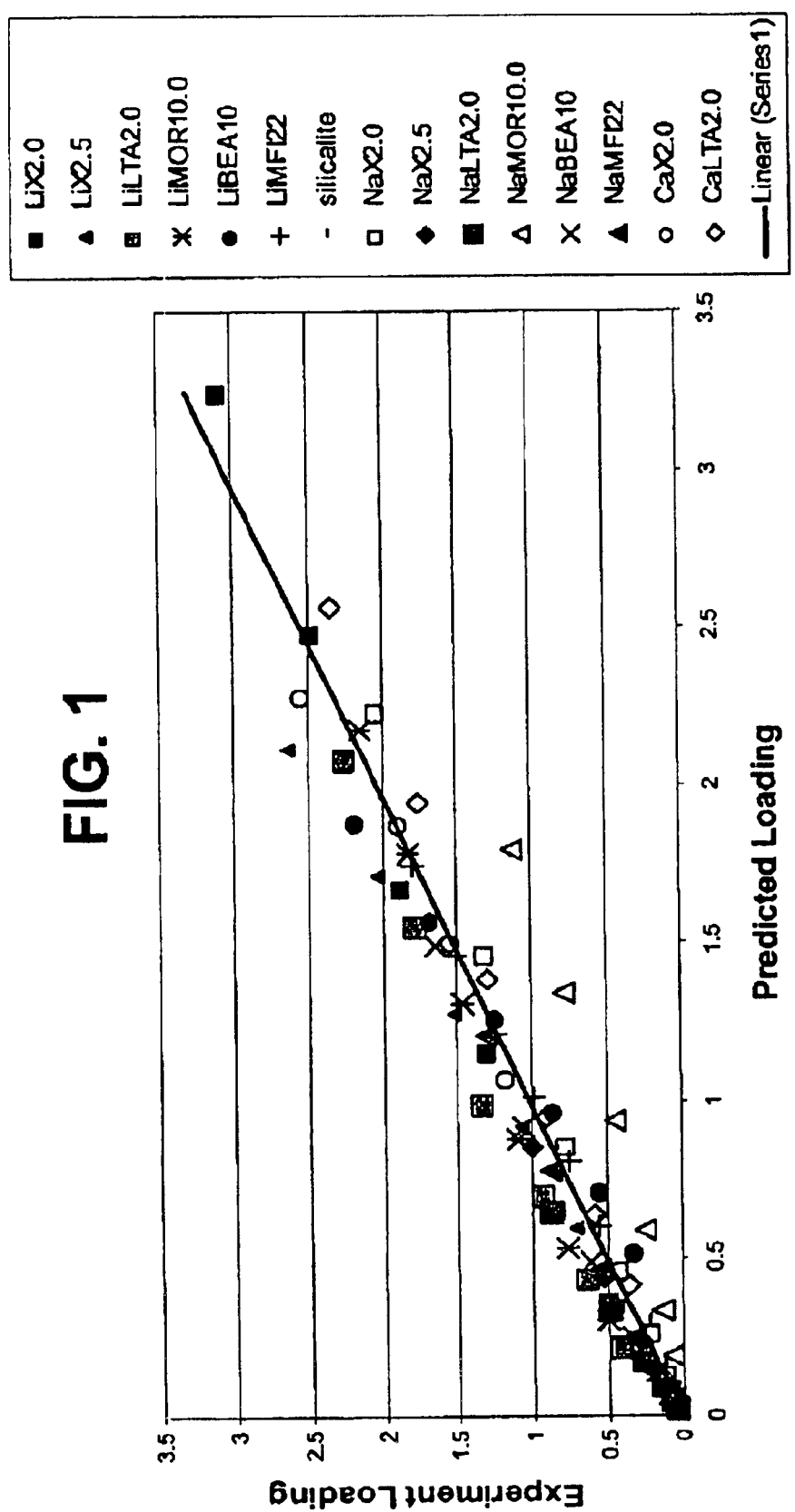
FIG. 1 is a scatter plot of experimental versus predicted $N_2$ loadings for various zeolites.

As stated, one embodiment of the present invention is a method for predicting zeolite structures and specifically the cation locations in those structures. Generally the method involves carrying out calculations to determine the lowest potential energy positions and distribution of the cations, determining the interaction of the cations with the framework atoms to finally obtain an optimized zeolite structure.

Methods which have been used in the past to predict zeolite structures begin with a three-dimensional potential energy grid of the crystallographic unit cell of the zeolite. These types of grids are well-known and can be constructed using a Lennard-Jones 6-12 potential to represent dispersion, and atomic mono poles to model the electrostatics. These grids can be constructed using commercial software such as Molecular Simulations, Inc. (now Acellrys) cation location program which is part of its Cerius 2 molecular modeling package or other non-commercial available programs. It should be pointed out that the various programs available will not necessarily give equivalent results.

Having obtained the grid and sorted it according to potential energy, one cation at a time is placed on the vertices of the grid and the lowest energy position of that cation is determined. This process is continued until enough cations are placed on the vertices which will neutralize the total negative charge on the zeolite framework.

The next step in the method involves having one cation (C1) jump from a first position (P1) up to 6Å in a random direction to a second position(P2). The energy of this new cation distribution is evaluated. The cation (C2) at position P1' closest to P2 of C1 is bumped away to another position (P2') a distance which is twice the distance as the original distance from P2 of C1 to P1' of C2 and along the C1(P2) to C2(P1') vector. That is, ·2*(P2–P1')·=·P2'–P1'·. Previous attempts to determine zeolite structures, have moved only one cation at a time whereas in the instant method, two cations are moved with the second cation being bumped by the first cation. This bumping technique is carried out on all the cations which simulates the simultaneous motion of all the cations. Using combinatorial minimization techniques, the potential energy of each of the bumped distributions is evaluated in order to find the lowest potential energy distribution. The combinatorial minimization technique is carried out until the average energy of the entire run converges to four significant figures. Usually, this means carrying out the bumping technique via combinatorial minimization for about 50,000 repetitions up to 5 million repetitions. The exact number is determined by increasing the repetitions in given increments and when the number of repetitions which leads to a convergence is determined, that number is increased by a factor of 5–10 to insure that convergence is obtained. The lowest energy cation distribution from the run is used in the next step.

This lowest energy cation distribution is now placed on an initial fixed zeolite geometry. The initial zeolite geometry or framework is obtained by first predicting an all silica framework and then randomly substituting aluminum for silicon into the framework to arrive at the desired $SiO_2/Al_2O_3$ ratio, with the restriction of Loewenstein's rule. Since, there is interaction between the extra framework cations and the framework silicon and aluminum atoms, molecular mechanics is next used to determine the lowest energy positions of the cations. This is easily done using commercial software DISCOVERS™ or OFF™ distributed by Accelrys or GULP developed by Professor J. D. Gale. See, J. Chem Soc., Faraday Trans., 93, (1997) 629 and www.gulp.curtin.edu.au. Once the lowest energy cation positions are found, those cations which are within 0.1Å of their special positions are moved to those positions. A special position is when an atom lies on a symmetry element that does not contain a translation component, i.e. an inversion center, a reflection plane or a rotation axis. Based on the positions of all the cations, the symmetrically equivalent sites are generated. Combinatorial minimization techniques, with bumping (as described above) is used to determine the minimum energy for the cations on the sites.

Since the cations interact with the framework atoms, any change in the cation distribution will affect the framework. Therefore the next step in the method is to determine the lowest energy geometry of the framework. This can be done using programs GULP, DISCOVER or OFF. Simultaneously, site occupation of the cations is obtained by determining the closest local minima for the cations. The optimized geometry and cation distribution provides a new zeolite structure. The entire method described above is now repeated at least one more time in order to obtain convergence of the new zeolite structure. It has been found that only one other iteration is required to obtain convergence of the structure, but in certain cases more than one iteration might be required.

The optimized zeolite geometry, cation distribution and cation positions, i.e. zeolite structure, obtained above can now be used to calculate and predict adsorption isotherms for various gases. The adsorption istherms are obtained by introducing a gas molecule into the zeolite structure using a biased-Grand Cononical Monte Carlo technique which contains electrostatic and dispersion interactions between the gas molecule and the zeolite. The electrostatic interaction between the zeolite and the gas molecules is obtained using a multipolar expansion of the charge distribution from a band structure calculation of the zeolite. The dispersion interaction between the zeolite and gas molecules is obtained using a Morse-Spline-Van der Walls (MSV) potential fit to experimental data. Using this Monte Carlo technique at various pressures (and constant temperature) predicts the loading of the gas molecules in the zeolite. It should be pointed out that the determination of an adsorption isotherm can be done independently of determining a zeolite geometry by simply using a known zeolite geometry. Similarly, having obtained an optimized geometry for a zeolite it can be used for purposes other than determining an adsorption isotherm such as calculating heats of sorption and the activity and selectivity of zeolite catalysts.

The methods of the present invention described above can be embodied in the form of computer implemented processes or programs and apparatuses for practicing those processes. The present invention can also be embodied in the form of computer program code containing instructions embodied in tangible media such as floppy diskettes, CD-ROMs, hard drives, or any other computer readable storage medium, wherein when the computer program code is loaded into and executed by a computer, the computer becomes an apparatus for practicing the invention. The present invention can also be embodied in the form of computer program code, whether stored in a storage medium, loaded into and/or executed by a computer, or transmitted over some transmission medium, such as over electrical wiring or cabling through fiber-optics, or via electromagnetic radiation, wherein, when the computer program code is loaded into and executed by computer, the computer becomes an apparatus for practicing the invention. When implemented on a general-purpose microprocessor, the computer program code segments configure the microprocessor to create specific logic circuits.

The following examples are presented to more fully illustrate the invention. It is understood that the examples are only by way of illustration and are not intended as an undue limitation on the broad scope of the invention as set forth in the appended claims.

EXAMPLE 1

The method of the present invention was used to predict the location of cations in various zeolites and compare them to known experimental results. The first comparison was with a zeolite having the faujasite (FAU) topology known as zeolite X. The FAU framework is constructed from double six-rings connected by four-rings. These building units also form ·-cages and supercages. Only cations in the supercages are accessible to sorbates. Alkali and alkaline earths occupy four types of sites in faujasite. Site SI is located in the center of the hexagonal prism. Site SI' is located in the faces of hexagonal prisms inside the ·-cage. Site SII is located in hexagons which are not the face of a hexagonal prism. This site is near the boundary between the ·-cage and the supercage. Site SIII is in the supercage and has been defined to be the center of the four ring connecting the double six-rings. Site SIII' is also in the supercage and has been defined to be in the plane of twelve ring bridging two oxygen atoms. These general definitions cover all the observed sites for cations in dehydrated faujasite.

Smith has proposed a model for the order of site filling in FAU as one increases the number of alkali (or alkaline earth) cations in a unit cell. Increasing the number of cations is equivalent to decreasing the $Si/Al_2$ ratio. Cations first occupy site I until all 16 SI sites are occupied. Cations then go into site SII until all 32 SII sites are occupied. Each additional cation now goes into a SI' and simultaneously moves the adjacent cation in SI to the adjacent SI'. Therefore 16 additional cations will occupy SI' moving 16 cations originally in SI to SI'. Once all the six rings in the FAU contain cations, additional cations occupy sites in the supercage (SII or SIII'). The Smith model is derived from dozens of studies and is generally accepted.

A comparison between experimental and theoretical cation distributions for NaFAU is shown in Table 1.

TABLE 1

Comparison of Results for NaFAU

| $Si/Al_2$ Ratio | Method | Unit Cell Volume (Å$^3$) | SI | SI' | SII | SIII | SIII' |
|---|---|---|---|---|---|---|---|
| 2.00 | Theory | 15821 | | 32.0 | 32.0 | | 32.0 |
| 2.41 | EXP* | 15718 | | 32.0 | 32.0 | | 24.0 |

*The experimental values were obtained from G. Vitale et al. J. Phys. Chem. 101 (1997) 4559.

EXAMPLE 2

Experimental and predicted (this invention) cation positions for LiFAU are presented in Table 2. Positions according to the present invention were determined for FAU having a $Si/Al_2$ of 2.0 and 2.56. Experimental results were obtained from the references listed at the bottom at Table 2.

TABLE 2

Comparison of Predicted Cation Distribution to Experiment and Distribution for LiFAU

| $Si/Al_2$ Ratio | Method | Unit Cell Volume (Å$^3$) | SI | SI' | SII | SIII | SIII' |
|---|---|---|---|---|---|---|---|
| 2.00 | Theory | 15192 | | 32 | 32 | | 32 |
| 2.00 | Exp[1] | 15076 | | 32 | 32 | 15.4 | 16.3 |
| 2.00 | Exp[2] | 15061 | | 29 (31.3) | 33 (33.5) | 34 (22.6) | |
| 2.56 | Theory | 15171 | | 32 29 | 32 32 | | 20 24 |
| 2.50 | Exp[2] | 15007 | | 29 (23.5) | 32 (30.4) | | (9.6) |

[1] J. Plevert, F. D. Di Renso, F. Fajula, G. Chiari, J. Phys. Chem. B 100 (1997) 10340.
[2] M. Feuerstein, R. F. Lobo, Chem. Mater. 10 (1998) 2197

The data in Table 2 shows good agreement between those positions derived from this invention and the experimentally determined positions. Note that there is disagreement among the experimentally determined positions as to which sites are filled in the supercage. However, it is observed that the total number of cations in the supercage is the same for both experimental determinations and that of the invention.

EXAMPLE 3

Experimental and predicted (this invention) cation distribution for CaFAU are presented in Table 2. As before, there is good agreement between the results of this invention and the experimental results.

TABLE 3

Comparison of Predicted and Observed Cation Distributions CaFAU

| Phase | $Si/Al_2$ Ratio | Method | Unit Cell Volume (Å$^3$) | SI | SI' | SII |
|---|---|---|---|---|---|---|
| CaFAU | 2.00 | Theory | 15995 | 16.0 | | 32.0 |
| | 2.00 | Exp.[1] | 15842 | 11.9 | 5.0 | 31.1 |
| | 2.17 | Exp.[2] | 15670 | 16.0 | | 30.0 |
| | 2.36 | Theory | 15776 | 16.0 | | 28.0 |
| | 2.90 | Exp.[3] | 15776 | 13.0 | 5.0 | 25.0 |

[1] G. Vitale, L. M. Bull, R. E. Morris. A. K. Cheetham, B. H. Toby, C. G. Coe, J. E. MacDougall, J. Phys. Chem. 99 (1995) 16087.
[2] Y. H. Yeom, S. B. Jang, Y. Kim, S. H. Song, K. Seff, J. Phys. Chem. B 101 (1997) 6914.
[3] D. H. Olsen, J. Phys. Chem. 72 (968) 1400

EXAMPLE 4

This example presents a comparison for Linde Type A (LTA) zeolites. The unit cell of LTA contains 64 six rings, 24 eight rings and 96 four rings which can serve as sites for cations. Smith's rule for LTA would predict that the six rings would fill first (SI) and then the eight rings (SII). There are more cations than six and eight rings for LTA with Si/Al2 ratios less than 2.3. Smith has assigned this extra site to the four rings (SIII). This is consistent with what is observed experimentally in LTA. The cation distribution from the method of the invention and experimentally determined are presented in Table 4.

TABLE 4

Comparison of Experimentally Observed and Predicted Cation Distribution for Various LTA Zeolites

| Phase | Si/Al$_2$ Ratio | Method | Unit Cell Volume (Å$^3$) | Six Ring | Eight Ring | Four Ring |
|---|---|---|---|---|---|---|
| NaLTA | 2.00 | Theory | 14909 | 64.0 | 24.0 | 8.0 |
|  | 2.00 | Exp[1] | 14814 | 62.2 | 23.2 | 6.3 |
| LiLTA | 2.00 | Theory | 14401 | 64.0 | 32.0 |  |
| CaLTA | 2.00 | Theory | 15037 | 48.0 |  |  |
|  | 2.00 | Exp[2] | 14598 | 44.8 |  |  |

[1] J. J. Pluth, J. V. Smith, JACS 102 (1980) 4704
[2] J. J. Pluth, J. V. Smith, JACS 105 (1983) 1192

The data in Table 4 once again show that there is good agreement between the predicted distribution and experimental distribution. Table 4 also shows the predicted distribution for LiLTA which indicates that it is different from that of NaLTA.

EXAMPLE 5

The cation distribution for mordenite (MOR) was also determined according to the invention and compared to experimental results. Mordenite does not contain six rings or any sodalite cages like FAU and LTA. These results are presented in Table 5.

TABLE 5

Comparison of Predicted and Observed Cation Distributions for Mordenite

| Phase | Si/Al$_2$ Ratio | Method | Unit Cell Volume (Å$^3$) | Number of Cations per Unit Cell | | |
|---|---|---|---|---|---|---|
|  |  |  |  | I' | IV | VI |
| NaMOR | 10.00 | Theory | 2739.00 | 4.0 | 4.0 | 0.0 |
|  | 9.29 | Exp* | 2722.38 | 3.1 | 2.6 | 1.5 |
| LiMOR | 10.00 | Theory | 2743.00 | 4.0 | 4.0 | 0.0 |

*J. L. Shlenker, J. J. Pluth, J. V. Smith, Mat. Res. Bull. 14 (1979) 751

The present method predicts that sites I' and IV are fully occupied whereas the experimental results indicate that there are less cations in sites I' and IV and that site VI is also occupied. However, the authors who determined the positions by x-ray diffraction stated that not all the cations were found and there was considerable disorder in the crystal used. This could account for the lower numbers in sites I' and IV. The cations in site VI may be due to the lower Si/Al$_2$ which increase the number of cations.

EXAMPLE 6

Isotherms for the zeolites in Table 6 were determined at room temperature and pressures of 25, 50, 100, 200, 400 and 800kPa using standard procedures. Isotherms were also predicted using the method of the invention described above.

TABLE 6

Zeolites for Which Isotherms Were Determined

| | | | |
|---|---|---|---|
| LiFAV (2.0) | LiFAV (2.5) | LiMOR (10.0) | LiLTA (2.0) |
| LiBEA (10.0) | LiMFI (22.0) | NaFAV (2.0) | NaFAV (2.5) |
| NaLTA (2.0) | NaMOR (10.0) | NaBEA (10.0) | NaMFI (22.0) |
| CaFAU (2.0) | CaLTA (2.0) | Silicalite* | |

*The pressures for silicalite were 3.125, 6.25, 12.5, 25, 50 and 100 kPa

A scatter plot of the experimental versus predicted N$_2$ loadings is presented in FIG. 1 and shows good agreement.

Figure 2:
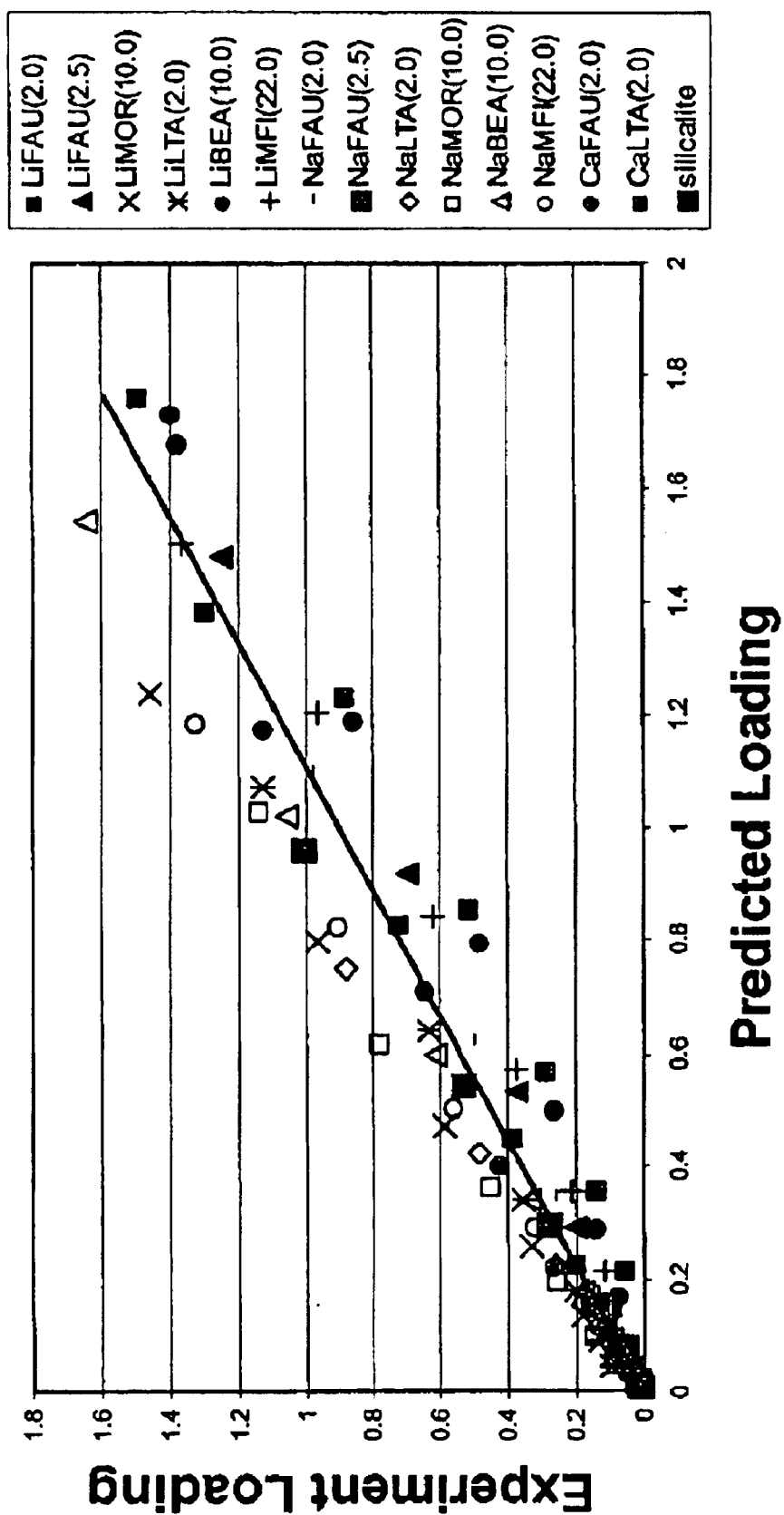
FIG. 2 is a scatter plot of experimental versus predicted $O_2$ loadings for various zeolites.
Figure 3:
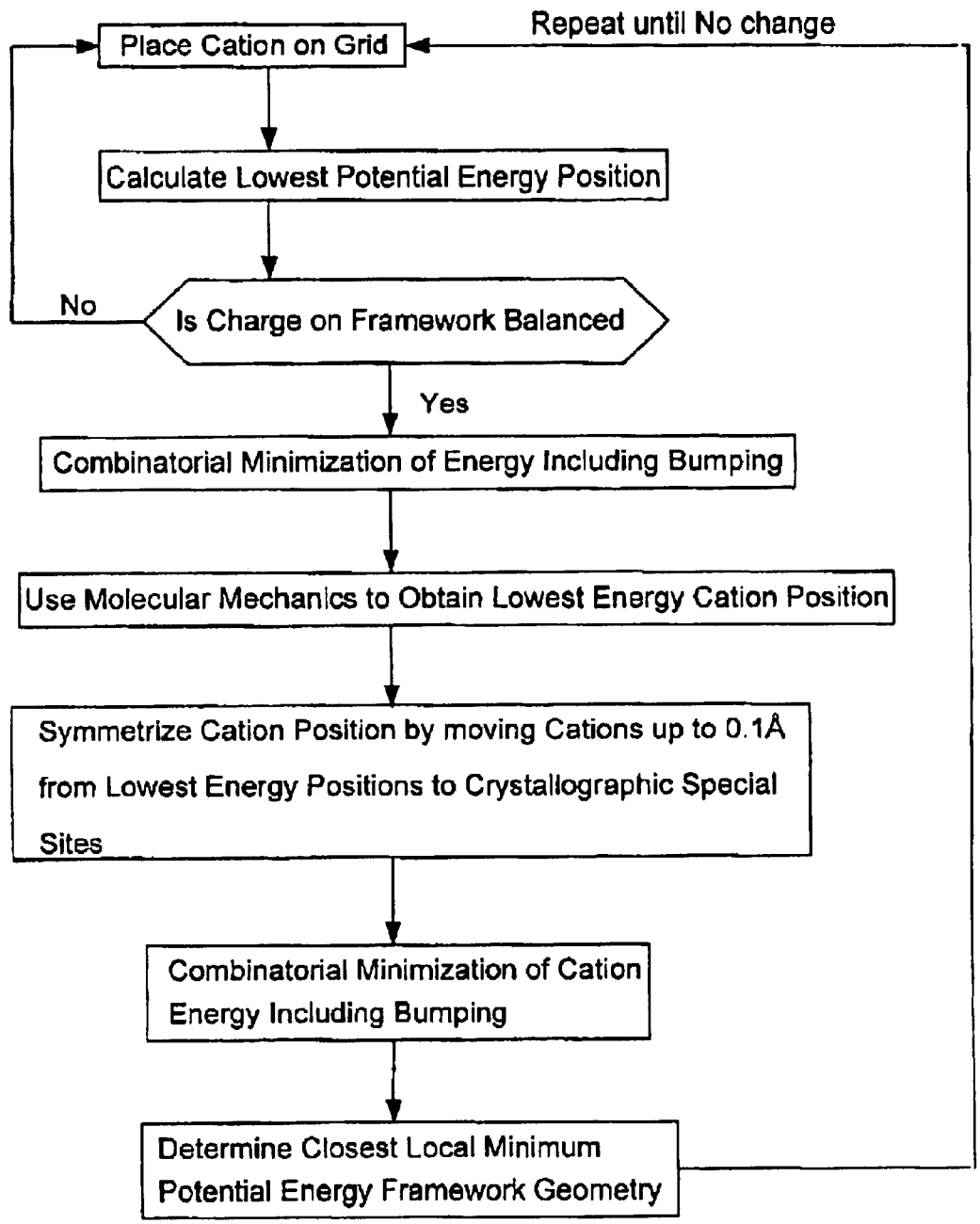
FIG. 3 is a flow diagram showing the steps in the present invention.

Similarly, FIG. 2 presents experimental versus predicted O$_2$ loadings. Again good agreement is observed.

I claim as my invention:

1. A method for determining a zeolite structure comprising a three-dimensional framework of AlO$_2$ and SiO$_2$ tetrahedral units and extra-framework cations, the method comprising:

a) placing one cation at a time onto vertices of a grid and calculating the lowest potential energy position for the cation and continuing to add cations until the negative charge of the framework is balanced;

b) bumping two cations during each step of a combinatorial minimization technique to obtain the lowest potential energy distribution of all the cations;

c) performing molecular mechanics calculations to obtain the lowest energy cation positions on a fixed zeolite geometry for the cation distribution of step (b);

d) moving each cation which is within 0.1Å of its special position, to its crystallographic special position; generating the symmetrically equivalent sites from the cation positions of all the cations and determining the minimum energy for the cations on the sites using combinatorial minimization techniques, with bumping;

e) optimizing the geometry of the framework and cation sites simultaneously to the closest local minimum; and f) repeating steps (a) to (e) at least once to obtain an optimized zeolite structure.

2. A computer readable storage medium containing computer executable code for instructing a computer to operate as follows:

a) placing one cation at a time onto vertices of a grid and calculating the lowest potential energy position for the cation and continuing to add cations until the negative charge of the framework is balanced;

b) bumping two cations during each step of a combinatorial minimization technique to obtain the lowest potential energy distribution of all the cations;

c) performing molecular mechanics calculations to obtain the lowest energy cation positions on a fixed zeolite geometry for the cation distribution of step (b);

d) moving each cation which is within 0.1Å of its special position, to its crystallographic special position; generating the symmetrically equivalent sites from the cation positions of all the cations and determining the minimum energy for the cations on the sites using combinatorial minimization techniques, with bumping;

e) optimizing the geometry of the framework and cation sites simultaneously to the closest local minimum; and f) repeating steps (a) to (e) at least once to obtain an optimized zeolite structure.

3. An executable code storage device readable by a computer, tangibly embodying a computer instructing said computer to perform a process for determining cation in a zeolitic structure comprises:

a) placing one cation at a time onto vertices of a grid and calculating the lowest potential energy position for the cation and continuing to add cations until the negative charge of the framework is balanced;

b) bumping two cations during each step of a combinatorial minimization technique to obtain the lowest potential energy distribution of all the cations;

c) performing molecular mechanics calculations to obtain the lowest energy cation positions on a fixed zeolite geometry for the cation distribution of step (b);

d) moving each cation which is within 0.1Å of its special position, to its crystallographic special position; generating the symmetrically equivalent sites from the cation positions of all the cations and determining the minimum energy for the cations on the sites using combinatorial minimization techniques, with bumping;

e) optimizing the geometry of the framework and cation sites simultaneously to the closest local minimum; and f) repeating steps (a) to (e) at least once to obtain an optimized zeolite structure.

* * * * *